US00PP08161P

United States Patent [19]

Egger

[11] Patent Number: Plant 8,161

[45] Date of Patent: Feb. 23, 1993

[54] GAZANIA PLANT CALLED "MOORPARK YELLOW"

[75] Inventor: Janet N. Egger, Wilsonville, Oreg.

[73] Assignee: Mitsuwa Nursery, Inc., Moorpark, Calif.

[21] Appl. No.: 745,459

[22] Filed: Aug. 14, 1991

[51] Int. Cl.[5] ..... A01H 5/00

[52] U.S. Cl. ..... Plt./87.14

[58] Field of Search ..... Plt./87.14

[56] References Cited

U.S. PATENT DOCUMENTS

P.P. 4,775 10/1981 Enright ..... Plt. 87.14
P.P. 5,795 11/1986 Ono ..... Plt. 87.14
P.P. 5,796 11/1986 Ono ..... Plt. 87.14
P.P. 5,797 11/1986 Beimel ..... Plt. 87.14
P.P. 7,493 4/1991 Egger et al. ..... Plt. 87.14

*Primary Examiner*—James R. Feyrer
*Attorney, Agent, or Firm*—Roylance, Abrams, Berdo & Goodman

[57] ABSTRACT

A new and distinct Gazania plant having large yellow banded flowers and green foliage and characterized by its vigorous growth and trailing habit.

1 Drawing Sheet

BACKGROUND OF THE INVENTION

The present invention relates to a new and distinctive cultivar of *Gazania rigens* hybrid and referred to commercially by the cultivar name 'Moorpark Yellow'. *Gazania rigens* 'Moorpark Yellow' was developed by controlled breeding using breeding plant #51-2 as the seed parent and breeding plant #46B-4 as the pollen parent.

BRIEF DESCRIPTION OF THE INVENTION

*Gazania rigens* 'Moorpark Yellow' is a perennial trailing groundcover with outstanding vigor, hardiness, green leaves and numerous large, showy yellow flowers with a black band that bloom from February through December in southern California. Its very large flowers that open early in the morning combined with its excellent vigor are believed to be a substantial step forward and an important advantage for *Gazania rigens* 'Moorpark Yellow' as compared to all other yellow flowering trailing Gazania groundcovers.

DESCRIPTION OF THE DRAWING

The accompanying color photograph, forming a part of this disclosure, was taken in the summer of 1991 in Somis, Calif., and shows a close-up of *Gazania rigens* 'Moorpark Yellow' growing in a 5 gallon can; the view more or less straight down into the plants. The photograph shows the typical flower and foliage form and color as true as is reasonably possible in this type of color photograph.

Comparison of *Gazania rigens* 'Moorpark Yellow' with Other Commercial Yellow Gazania Groundcovers with Green Leaves The primary distinguishing features of the *Gazania rigens* 'Moorpark Yellow' are its large yellow flowers with black bands and its vigorous growth. To the inventor's knowledge there are only two other yellow flowering Gazania groundcovers with green leaves and yellow flowers with black bands. These other Gazanias are *Gazania rigens* 'Sunrise' and *Gazania rigens* 'Mitsuwa Super Clump', illustrated in U.S. Plant Pat. No. 5,795 issued Nov. 4, 1986. In comparison to *Gazania rigens* 'Sunrise', *Gazania rigens* 'Moorpark Yellow' has much more vigor, much larger, flatter flowers which open earlier, larger leaves, greater spread and height and is more frost hardy.

In comparison to *Gazania rigens* 'Mitsuwa Super Clump', illustrated in U.S. Plant Pat. No. 5,795 issued Nov. 4, 1986, *Gazania rigens* 'Moorpark Yellow' has larger, flatter, darker flowers which open earlier, bigger leaves and a growth habit which is trailing rather than clumping.

Compared to *Gazania rigens* 'Mitsuwa Yellow', the most commonly planted Gazanias groundcover in California, *Gazania rigens* 'Moorpark Yellow' has larger flowers with a golden color and a black ring around the flower center. They both trail vigorously.

DETAILED DESCRIPTION

The following is a detailed description of *Gazania rigens* 'Moorpark Yellow' based on plants produced under commercial practices outdoors at Mitsuwa Nursery, Moorpark, Calif. Color references are made to The Royal Horticultural Society Colour Chart, except where the context indicates a term having its ordinary dictionary meaning.

Parentage: A controlled breeding cross with Gazania breeding plant #51-2 as the seed parent and Gazania breeding plant #46B-4 as the pollen parent.

Plant form: Plants are vigorous growing trailing groundcover.

Habit of growth: Plants are decumbent, spread rapidly to approximately 1½ meter in diameter. Plants form a dense carpet to approximately 17 cm in height.

Foliage: Foliage is a medium green with alternate leaves and clasping petioles.

1. *Size.*—Mature leaves are approximately 14½ cm in length.
2. *Shape.*—Leaves vary from simple oblanceolate (to 17 mm in width) to pinnately six lobed (to 25 mm in width).
3. *Texture.*—Leaves are glabrous above and tomentose below.
4. *Margin.*—Serrulate.

5. *Color.*—Topside — 147 A. Underside — 155 D.

Flowering description:

1. *General.*—The flowers are a deep yellow with a black band or ring around the flower center at the base.

2. *Habit.*—The flower heads arise from leaf axils on peduncles to approximately 13 cm in length.

3. *Season of bloom.*—Varies with the climate. In Moorpark, Calif., heavy bloom occurs from approximately late February to early December.

4. *Flower parts.*—a. Flower heads measure to approximate 85 mm across. The disc flowers in the center measure approximately 15 mm across. b. Ray petals measure up to approximately 52 mm in length and up to approximately 13 mm in width. The base of each ray petal has a black spot measuring approximately 4 mm wide, and which may or may not have a small white dot in the middle. These black spots form the band or ring at the flower base. The underside of each ray petal has a longitudinal lighter yellow section down the center between the two main veins and a dark blue-black spot at the base. c. There are 18 to 20 ray petals per flower head.

5. *Color.*—Ray petal, topside — 14B. Ray petal, bottomside, edges — 14A. Ray petal, bottomside, center — 11C.

Disease resistance: No disease problems have been found in *Gazania rigens* 'Moorpark Yellow'. In the fields at Mitsuwa Nursery, *Gazania rigens* 'Moorpark Yellow' has shown good disease tolerance.

Hardiness: *Gazania rigens* 'Moorpark Yellow' has gone through two frost tests at Mitsuwa Nursery to qualify for patentability. It has proven to be more frost tolerant than *Gazania rigens* 'Mitsuwa Yellow', the most commonly planted yellow training Gazania in California.

Propagation: Asexual reproduction of the new and distinct variety has been accomplished by stem cuttings. The resulting plants have shown that the above-mentioned unique features of this new Gazania are stable and reproduce true to type in each of the successive propagations. *Gazania rigens* 'Moorpark Yellow' roots in about 2–3 weeks in warm conditions.

I claim:

1. A new and distinct cultivar of Gazania as described and illustrated, particularly characterized by its large yellow banded flowers, green foliage, vigorous growth and trailing habit.

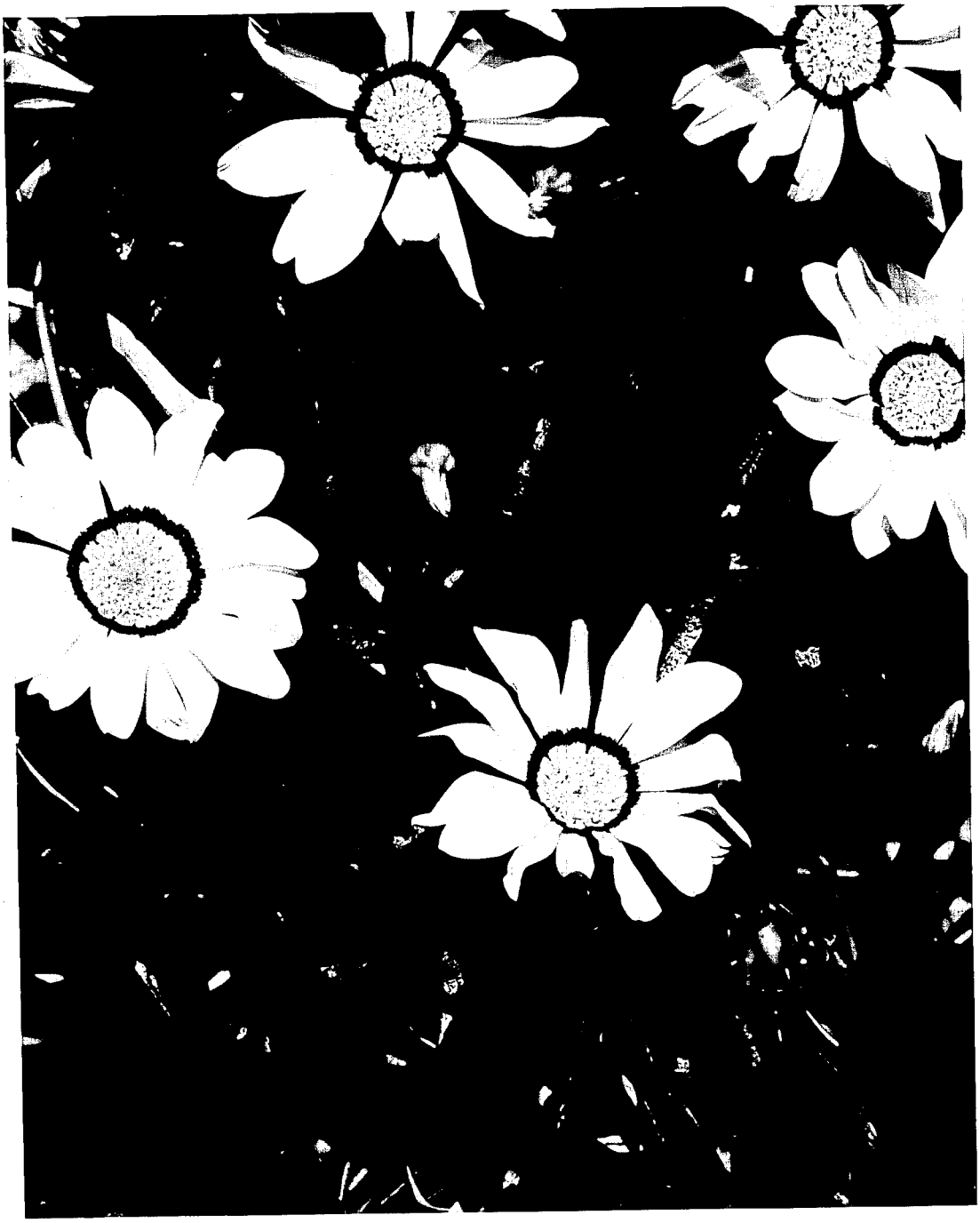

* * * * *